United States Patent [19]

Okada

[11] Patent Number: 5,601,525

[45] Date of Patent: Feb. 11, 1997

[54] HARD-TYPE ENDOSCOPE APPARATUS

[75] Inventor: Mitsumasa Okada, Hachioji, Japan

[73] Assignee: Olympus Optical Co., Ltd., Tokyo, Japan

[21] Appl. No.: 389,017

[22] Filed: Feb. 15, 1995

[30] Foreign Application Priority Data

Apr. 11, 1994 [JP] Japan .................................. 6-072074

[51] Int. Cl.⁶ ........................................................ A61B 1/06
[52] U.S. Cl. ........................ 600/160; 600/138; 600/171; 600/181; 359/435
[58] Field of Search ...................... 600/138, 160, 600/162, 163, 181, 171, 133, 105, 109, 114; 385/902; 359/433, 434, 435; 606/15, 16

[56] References Cited

U.S. PATENT DOCUMENTS 3,257,902  6/1966  Hopkins ................................. 600/163
4,306,546 12/1981 Heine et al. ................................ 128/6
5,078,773  1/1992 Thomas ....................................... 65/37
5,359,453 10/1994 Ning ......................................... 359/435
5,423,312  6/1995 Siegmund et al. ....................... 600/109
5,488,990  9/1995 De Faria-Correa ................ 600/105 X

FOREIGN PATENT DOCUMENTS 3912720  10/1990  Germany .
61-47913  3/1986  Japan .
61-64421  4/1986  Japan .
WO93/17362  9/1993  WIPO .

*Primary Examiner*—Richard J. Apley
*Assistant Examiner*—Beverly M. Flanagan
*Attorney, Agent, or Firm*—Frishauf, Holtz, Goodman, Langer & Chick

[57] ABSTRACT

A hard-type endoscope apparatus equipped with an inserting portion, a plurality of lenses inserted in the insertion portion, and a lens-barrel holding the lenses, includes a spacer pipe provided in the lens-barrel along the optical path of the lenses. The lens barrel is made of synthetic resin materials containing an additive. The additive forms matting irregularities on an inner surface of the tubular member.

10 Claims, 4 Drawing Sheets

HARD-TYPE ENDOSCOPE APPARATUS

BACKGROUND OF THE INVENTION

1. Field of the Invention

This invention relates to a hard-type endoscope apparatus having an observation optical system located in its insertion portion for transmitting an image to be observed to the side of its eye-piece portion via a plurality of lenses.

2. Description of the Related Art

In general, an observation optical system incorporated in an endoscope, in particular, in a hard type endoscope includes an objective system, a relay system and an eye-piece system, and comprises several tens of glass lenses. An image to be observed is transmitted to the side of the eye-piece system via those lenses.

FIG. 8 shows a prior art arrangement of glass lenses a employed in a general hard-type endoscope. The glass lenses a are generally inserted in a metal pipe (scope barrel) b so as to keep the optical axes of the lenses in line. Spacer pipes c are interposed between each adjacent pair of the lenses a for keeping them at regular intervals.

In many conventional cases, a metal pipe is used as the spacer pipe c. At the time of observation, a light beam passes through the spacer pipes c for enabling an image to be observed. Further, as is shown in FIG. 8, light beams $L_1$ and $L_2$ passing out of the field of view are reflected from inner surface portions of the spacer pipes c.

Since in the above-described general hard-type endoscope, the distance between each adjacent pair of the lenses a is relatively short, the reflected light beams $L_1$ and $L_2$ soon enter outer peripheral portions of the lenses a. The outer periphery of each lens, in general, is not completely polished, and has a relatively rough surface. Therefore, each of the reflected light beams $L_1$ and $L_2$ change to scattered light beams $L_3$ at the periphery of the lens and disappear. This being so, only subjecting the lens a to a reflection-preventing treatment can prevent the occurrence of flare in a picked-up image, without subjecting the inner surface of the spacer pipe c to any special reflection-preventing treatment.

Further, there is a conventional endoscope, in which the inner surface of the metal spacer pipe c is coated with a matting black film so as to prevent a light beam passing through the pipe for image observation, from being reflected from its inner surface.

On the other hand, attention has been paid to a disposable endoscope, and various improvements have been developed for the same. In this case, the reduction of the manufacturing cost is regarded as important. To this end, an optical component such as a lens, a light guide, etc. has been made of a resin, as is disclosed in PCT W093/17362.

Moreover, Japan Patent Application KOKAI Publication No. 61-47913 discloses a technique for forming the barrel of a zoom lens for video cameras of a resin in order to reduce its manufacturing cost. DE 3912720 discloses a technique for positioning a relay lens system by means of a thermally contractive tube. Furthermore, there are known a technique for integrally forming a resin lens and a space pipe as one body, and a technique for providing, in a pipe, flange means to define the distance between each adjacent pair of lenses aligned in the pipe.

It is considered to reduce the number of the lenses a of an observation system employed in a disposable hard-type endoscope so as to reduce the manufacturing cost of the endoscope, as compared with the conventional one equipped with several tens of lenses a.

In this case, however, the distance between each adjacent pair of the lenses a inevitably increases as in the endoscope disclosed in PCT W093/17362, and therefore relatively long spacer pipes c are necessary. In the case of using relatively long spacer pipes c, it is possible that scattered light, which is part of light indicative of an image to be observed, reflects from the inner periphery of the long spacer pipes c, and the reflection light is transmitted to the eye piece, thereby causing flare in the image.

In order to avoid the occurrence of flare, a black matting layer of black chrome, etc. is generally formed on the inner periphery of the spacer pipe c to prevent reflection of light therefrom. However, it is difficult to uniformly coat the overall inner periphery of the pipe with the black matting layer, since the spacer pipe is a thin pipe having its axial length formed much longer than its radial length.

Further, Japan Patent Application KOKAI Publication No. 61-64421 discloses a technique for forming the lens barrel of a camera of a resin in order to reduce its manufacturing cost. In this case, however, the lens barrel consists of a plurality of separate barrel elements, and hence is more expensive than a lens barrel which consists of a single barrel element. In addition, although the technique for coating the inner periphery of a spacer pipe with a black matting layer is applicable, for example, to a camera having a relatively large diameter, it is hard to apply to an endoscope having an inserting portion whose diameter is limited to a low value. Moreover, in the case of forming an axially-long thin pipe by injection molding of a synthetic resin, it is necessary to design a draft, etc. in a die, which makes it difficult to form the die.

As in the case of DE3912720 where the relay lens system is positioned by means of a thermally contractive tube, various improvements have been made to the spacer pipe c to reduce the manufacturing cost. However, no improvement has been made to prevent reflection of light from the inner periphery of the spacer pipe c thereby to prevent occurrence of flare in an image to be observed.

SUMMARY OF THE INVENTION

The present invention has been developed under the above-described circumstances, and aims to provide a hard-type endoscope apparatus in which the amount of scattered light reflected from the inner periphery of a lens barrel and guided to the side of an eye piece can be reduced, and which can be manufactured at low cost.

To attain the object, there is provided a hard-type endoscope apparatus equipped with an inserting portion, an observation optical system inserted in the insertion portion, and a lens-barrel holding the observation optical system, comprising:

a tubular member provided at least in the lens-barrel along an optical path of the observation optical system, the tubular member being made of synthetic resin materials containing an additive, the additive forming matting irregularities on the inner surface of the tubular member.

In the above structure, when observation light has struck the inner periphery of the tubular member, it is irregularly reflected from the matting irregularities of the inner periphery, thereby preventing the light reflected from the inner periphery of the tubular member from being transmitted to the side of the eye piece. As a result, occurrence of flare in a picked-up image is prevented.

In summary, in the endoscope apparatus of the invention, the amount of scattered light reflected from the inner periphery of the lens barrel and transmitted to the side of the eye piece can be reduced, and the apparatus can be manufactured at low cost.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Figure 1:
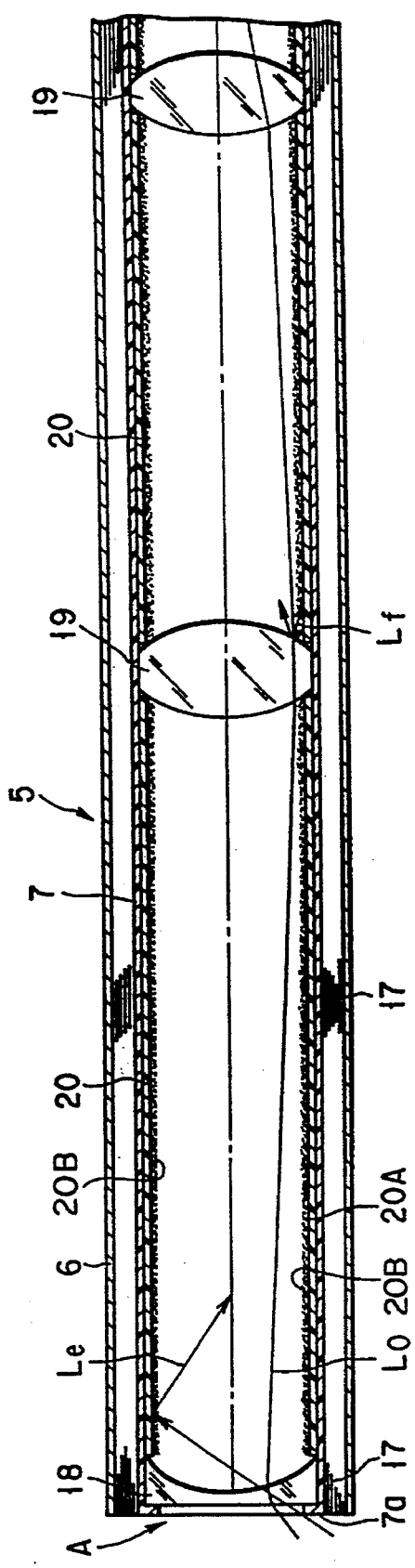
FIG. 1 is a longitudinal sectional view, showing an essential part of the inserting portion of a hard-type endoscope according to a first embodiment of the invention.

A first embodiment of the invention will be explained with reference to FIGS. 1 and 2. FIG. 2 is a schematic view, showing the overall structure of a disposable hard-type endoscope 1. The endoscope 1 has an inserting portion 5 to be inserted into the body of a patient, and a proximal end portion 2 connected to the inserting portion 5. The proximal end portion 2 has an eye-piece mounting portion 3, and a light guide connector 4 formed integral with the portion 3 as one body.

The inserting portion 5 includes an outer sheath 6 and an inner sheath (lens-barrel) 7 arranged concentric with the outer sheath 6. The proximal end of the outer sheath 6 is fitted in an outer sheath-attaching hole 2a formed in the proximal end portion 2.

An eye-piece-mounting hole 9 is formed in the proximal end portion 2, and receives therein an eye-piece unit 8. A female screw portion 10 is formed in an inner peripheral portion of the eye-piece-mounting hole 9. An inner sheath-fixing hole 2b is formed in an inner bottom portion of the eye-piece-mounting hole 9, and receives therein the proximal end of the inner sheath 7.

The eye-piece unit 8 has a substantially cylindrical unit case 11, and an eye piece 12 contained in the case 11. A stepped engagement portion 13 is formed at a substantially central portion of the inner periphery of the unit case 11, and stops an edge portion of the eye piece 12. The stepped engagement portion 13 consists of a hole having a diameter smaller than the outer diameter of the eye piece 12.

A male screw portion 14 is formed on an outer peripheral portion of the unit case 11, and engaged with the female screw portion 10 of the eye-piece-mounting hole 9. A spring-urging ring 15 is fixed to the outer periphery of the proximal end of the inner sheath 7.

The eye piece 12 is urged against the stepped engagement portion 13 by means of the spring-urging ring 15 and a torsion coil spring 16 in the unit case 11 of the eye-piece unit 8. Accordingly, the eye-piece unit 8 can be moved in the axial direction of the eye-piece-mounting hole 9 (in the direction of the optical axis of the eye piece 12) by rotating the male screw 14 of the unit case 11 engaged with the female screw 10 of the eye-piece-mounting hole 9, thereby changing the focal point of the eye piece 12.

A light guide 17 consisting of optical fibers for transmitting illumination light is inserted in an annular space between the outer and inner sheaths 6 and 7 of the inserting portion 5. The optical fibers of the light guide 17 are uniformly located in the overall annular space between the inner and outer sheaths 7 and 6. The light guide 17 has its distal end face fixed in the vicinity of an objective lens 18 secured to the distal end inner surface of the inner sheath 7. The proximal end of the light guide 17 extends into an inner portion of the proximal end portion 2, and is gathered into a bundle and connected to the light guide connector 4.

A plurality of lenses which constitute an observation optical system A, i.e., the objective lens 18 and a plurality of relay lenses 19, are fitted in the inner sheath 7. Further, as is shown in FIG. 1, a spacer pipe 20 is located between each adjacent pair of the objective lens 18 and the relay lenses 19 for separating them from each other.

The spacer pipe 20 is formed by cutting a long pipe 20A of a synthetic resin in accordance with the distance between each adjacent pair of lenses. The pipe 20A is formed by extrusion molding of a synthetic resin containing an additive. In a case where the pipe 20A is molded tubular, by extrusion molding, out of a synthetic resin containing, in particular, glass, the outer periphery of the pipe has a smooth surface as a result of being pressed by a mold. On the other hand, the inner periphery is not pressed by the mold, and hence glass particles appear thereon. The added glass particles provide a multiple of fine irregularities on the inner periphery of the pipe 20A. Thus, the inner periphery of the pipe serves as a matting rough surface on which light is hard to reflect.

The synthetic resin as a material of the pipe 20A is, for example, ABS, PC, PE, PVC, PP, PA, SAN, PET, PS, PMMA, POM, etc., and is not limited to any particular material. However, where it is necessary for the pipe to have a high resistance against a highly pressurized vapor for sterilization, the pipe is preferably made of a resin fluoride such as PTFE, PFA or FEP, or a heat resisting resin such as PEEK, PSF, modified PPO, PEI, phenol resin, PPS or epoxy resin. Further, the additive to be mixed into the materials of the synthetic resin is, for example, a glass fiber, a glass milled fiber, glass beads, a mixture thereof, a fiber, a fine powder other than glass such as a metal powder, etc.

The inner sheath 7 has its distal end bent inward, forming a bent portion 7a which holds a front edge portion of the objective lens 18. The objective lens 18 is rigidly held between the bent portion 7a of the inner sheath 7 and the spacer pipe 20.

The operation of the above-described structure will now be explained. At the time of observation using the hard-type endoscope 1, illumination light supplied from a light source connected to the light guide connector 4 of the proximal end portion 2 is guided to the distal end side of the inserting portion 5 through the light guide 17, and radiated forward.

An image to be observed is guided to the side of the eye-piece unit 8 via the observation optical system A. Specifically, light indicative of the image enters the objective lens 18 of the system A, passes the relay lenses 19, and reaches the eye piece 12. The image is viewed by the observer, directly or via a TV camera.

Figure 2:
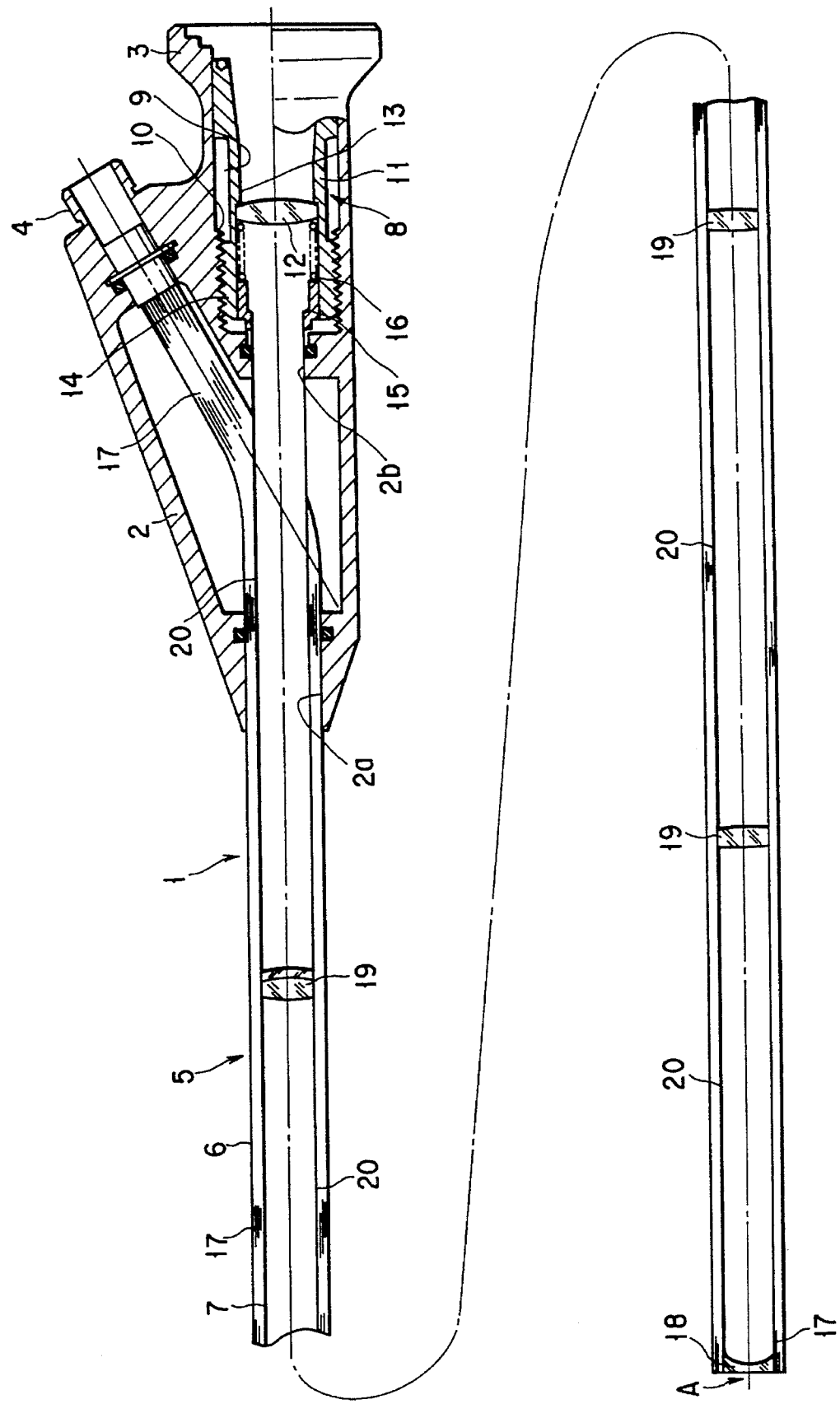
FIG. 2 is a longitudinal sectional view of the overall structure of endoscope of FIG. 1.

As is shown in FIG. 1, while light $L_0$ within the field of view of the eye piece 12 continuously passes the relay lenses 19 after entering the objective lens 18, it does not strike upon the inner peripheral surfaces of the spacer pipes 20.

On the other hand, light $L_e$ out of the field of view of the eye piece 12 strikes upon the inner peripheral surfaces of the spacer pipes 20. Since the inner peripheral surfaces of the pipes 20 have fine irregularities, 20B (shown in a sectional view thereof) the light having struck upon the inner peripheral surface irregularly reflects therefrom. This reduces the amount of those of a light beam $L_e$ out of the field of view of the eye piece 12 and light beams $L_f$ scattered on the surfaces of lenses, which are reflected from the inner peripheral surfaces and guided to an eye piece 12. As a result, a clear image with little flare can be transmitted.

In summary, the above-described structure has the following advantages:

The objective lens 18 and the relay lenses 19 are rigidly separated from each other by means of the spacer pipe 20 interposed between each adjacent pair of the lenses. The spacer pipes 20 comprise the long synthetic resin pipes 20A formed by extrusion molding of a synthetic resin containing an additive and cut in accordance with the distance between each adjacent pair of the lenses. The additive provides the inner periphery of the synthetic resin pipe 20A with matting irregularities. This being so, the amount of light guided to the eye piece 12 after reflecting from the inner periphery of the synthetic resin pipe 20A can be reduced, with the result that an image with little flare can be transmitted.

Moreover, among a glass fiber, a glass milled fiber, glass beads, etc., the glass milled fiber is most preferable as the additive to be mixed into the materials of the synthetic resin of the spacer pipe 20. This is because the glass milled fiber and the glass fiber are cheaper than the glass beads, and the glass milled fiber is thinner than the glass fiber. More specifically, the thinner glass milled fiber provides the inner periphery of the spacer pipe 20 with finer irregularities 20B and accordingly a higher matting effect than the glass fiber. Further, the thinner glass milled fiber enables the spacer pipe 20 to have a more accurate size.

In addition, light is prevented from reflecting from the inner periphery of the spacer pipe 20 formed by extrusion molding of the synthetic resin mixed with glass. This means that the use of the spacer pipe 20 constructed as above makes unnecessary complicated processes such as a process for forming irregularities on the inner periphery by, for example, applying sand thereto, and a process for coating the inner periphery. As a result, the manufacturing cost can be significantly reduced.

Furthermore, the overall long synthetic resin pipe 20A is formed at a time by extrusion molding, which is advantageous as compared with the case of forming each divisional portion of a long pipe by injection molding. The extrusion molding can also produce a pipe with an extremely thin thickness of e.g. 0.3 mm or less. Therefore, the extrusion molding is an optimal method for forming the lens-barrel of an endoscope whose diameter is limited.

As described above, since in the embodiment, the extrusion molding is employed, the axial length of the spacer pipe 20 is not limited, and the inner periphery of the pipe can have a good reflection-preventing effect.

Black is optimal as the color of the spacer pipe 20 for preventing reflection. However, the color can be selected relatively freely by changing the kind of additive to be mixed into the materials of a synthetic resin.

Since the spacer pipe 20 is formed by extrusion molding, the cross section of the lens-barrel which constitutes the observation optical system A is not limited to circle, but can be modified to an ellipsoidal, a triangle, a rectangle, a polygon, etc.

Also, mixing the materials of a synthetic resin with glass can eliminate drawbacks of synthetic resins such as low size accuracy, size change depending on temperature, etc. Thus, the synthetic resin containing glass has high size accuracy free from temperature, and high resistance against temperature. Since the lenses of the observation optical system A must have high size accuracy, the lens-barrel of the endoscope employing the spacer pipes 20 is optimal.

The lens-barrel which employs the spacer pipes 20 of a synthetic resin can be used not only to define the distances between lenses, but also to position a mask or to define the distance between the CCD of a video endoscope and a lens.

The additive to be mixed into the materials of a synthetic resin of the spacer pipe 20 is not limited to glass, but may be a ceramic fiber, a Kevlar fiber, milled fibers of them, or a powder of ceramic or boron.

Only to prevent reflection on the inner periphery of the resin lens-barrel, sand may be blasted onto the inner periphery, or irregularities 20B may be formed on the inner periphery by mixing a metal powder, as an additive, into a resin with high resistance against drugs, such as Teflon, to mold a resin lens-barrel, and dissolving the metal powder after molding.

Figure 3:
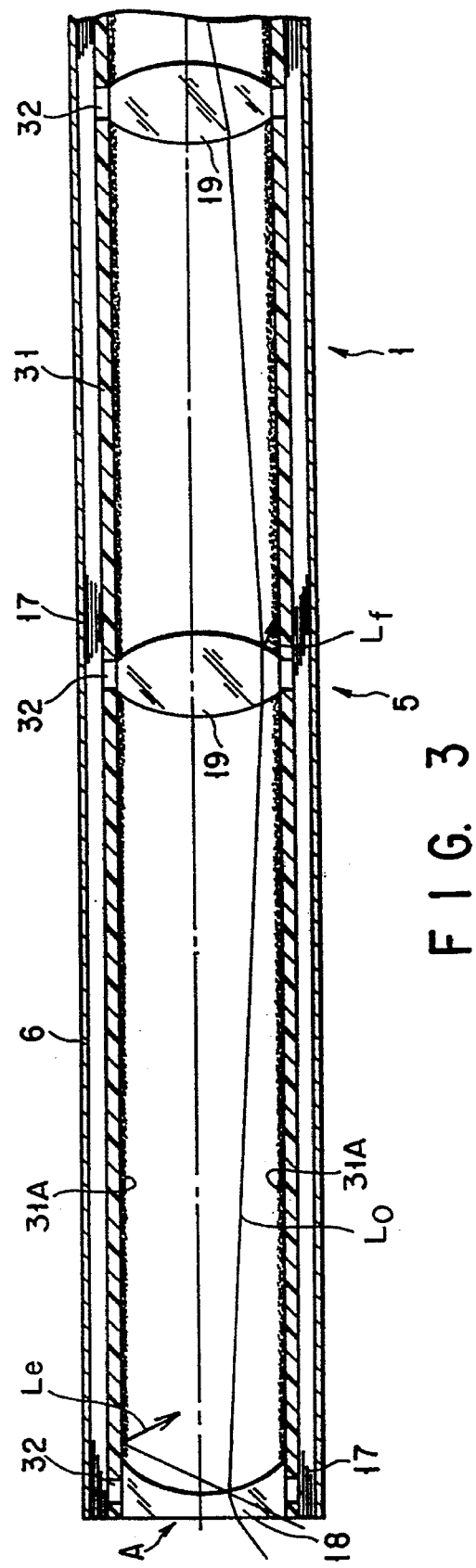
FIG. 3 is a longitudinal sectional view, showing an essential part of a second embodiment of the invention.

FIG. 3 shows a second embodiment of the invention. In this embodiment, an inner sheath (tubular member) 31 formed of a resin pipe containing glass is located in an inserting portion 5 of the disposable hard-type endoscope 1, an objective lens 18 and a plurality of lenses 19 are fixed in the inner sheath 31. The inner sheath 31 is molded by extrusion molding of a synthetic resin mixed with glass as an additive.

A light guide 17 is interposed between the inner sheath 31 and an outer sheath 6 of the inserting portion 5. A plurality of holes 32 are formed in the inner sheath 31 and filled with an adhesive, thereby fixing the objective lens 18 and the relay lenses 19.

Since the second embodiment employs the inner sheath 31 molded out of a glass-contained resin pipe by extrusion molding, the amount of those of light beams indicative of an image to be observed and having entered the objective lens 18, which are reflected from the inner sheath 31 and guided to an eye piece 12, can be reduced. More specifically, when a light beam $L_e$ out of the field of view of the eye piece 12 and light beams $L_f$ scattered on the surface of a lens have struck upon the inner periphery of the inner sheath 31, they irregularly reflect therefrom as a result of the presence of irregularities 31A provided on the inner surface of inner sheath 31. As a result, the amount of reflected light to be guided to the eye piece 12 is reduced. Thus, a clear image with little flare can be transmitted, as in the first embodiment.

Further, since in the second embodiment, the inner sheath 31 is formed of a resin pipe molded, by extrusion molding, out of a synthetic resin containing glass as an additive, no members corresponding to the spacer pipes 20 employed in the first embodiment are necessary. Therefore, the number of required components is much smaller than in the first embodiment, and accordingly the manufacturing cost can be reduced. Moreover, since the optical path is widened by the thickness of the spacer pipe 20, as compared with the first embodiment, a more bright observation optical system A can be provided.

Since the inner sheath 31 of the endoscope is very long in the axial direction relative to its radial length, it is impossible to coat the inner periphery of the sheath with a reflection-preventing film. However, in the second embodiment, a reflection-preventing effect is imparted in a simple manner and at low cost as a result of using the inner sheath 31.

Figure 4:
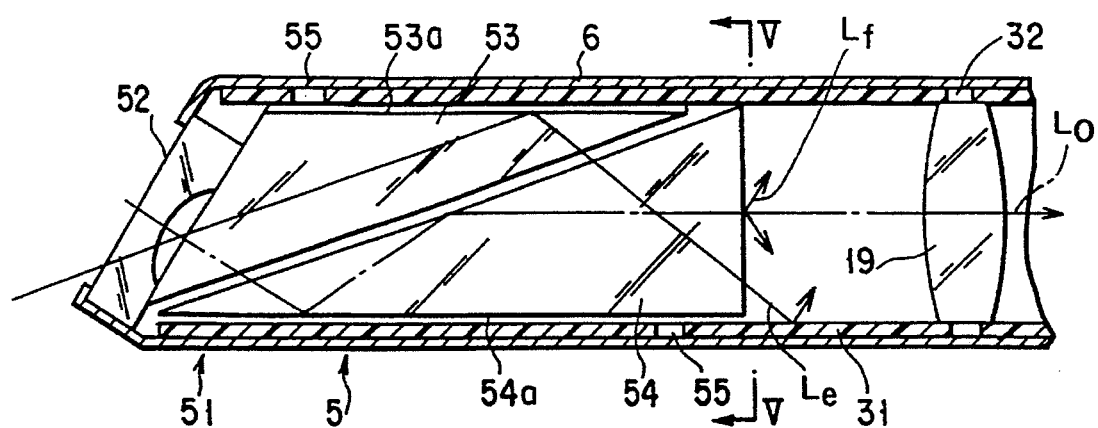
FIG. 4 is a longitudinal sectional view, showing an essential part of the inserting portion of a hard-type endoscope according to a third embodiment of the invention.
Figure 5:
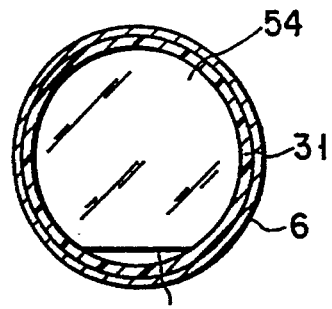
FIG. 5 is a view taken along lines V—V of FIG. 4.

FIGS. 4 and 5 show a third embodiment of the invention. The third embodiment differs from the second embodiment of FIG. 3 in that an objective optical system 51 for performing observation in an oblique direction is mounted at the distal end of the inserting portion 5 of the hard-type endoscope 1.

The objective optical system 51 has an end lens 52 obliquely located at the distal end of the outer sheath 6. A first prism 53 is provided in the inner sheath 31 such that the front surface of the prism 53 contacts the lens 52, and a second prism 54 is provided in the inner sheath 31 in contact with the first prism 53.

The prisms 53 and 54 respectively have reflection surfaces 53a and 54a obtained by cutting part of their circular cross sections. A plurality of holes 32 are formed in the inner sheath 31, and the relay lenses 19 are fixed thereto by means of an adhesive inserted through the holes 32. Further, a plurality of holes 55 are formed in the inner sheath 31, and the prisms 53 and 54 are fixed thereto by means of an adhesive inserted through the holes 55. It is desirable to adhere, to the inner sheath 31, those portions of the prisms 53 and 54 which are not located on the optical path.

Since the third embodiment employing the inner sheath 31 includes a resin pipe formed by extrusion molding of synthetic resin materials mixed with glass as an additive, as in the second embodiment, the amount of those of light beams indicative of an image to be observed and having entered the end lens 52 of the objective optical system 51, which are reflected from the inner sheath 31 and guided to an eye piece 12, can be reduced. More specifically, the amount of those of a light beam $L_e$ out of the field of view of the eye piece 12 and light beams $L_f$ scattered on the surface of a lens, which are reflected from the inner periphery of the inner sheath 31 and guided to the eye piece 12, can be reduced. As a result, a clear image with little flare can be transmitted, as in the first embodiment. Further, the same advantages as the second embodiment can be obtained.

Figure 6:
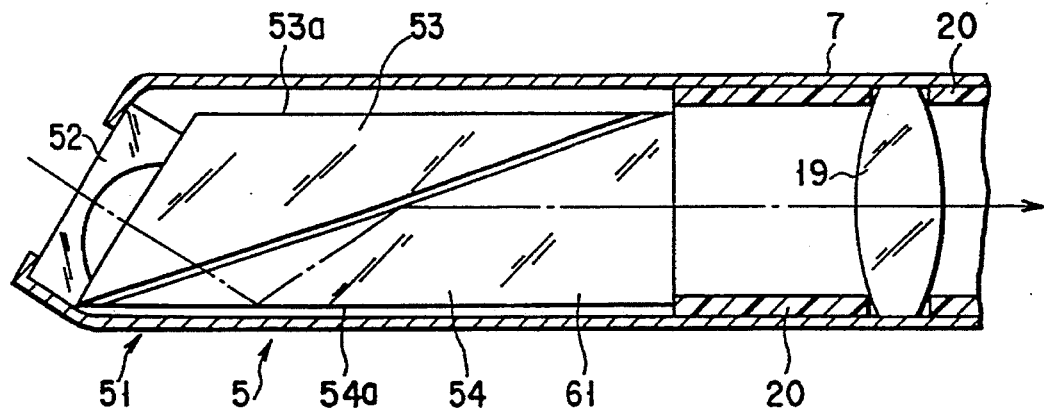
FIG. 6 is a longitudinal sectional view, showing an essential part of the inserting portion of a hard-type endoscope according to a fourth embodiment of the invention.

FIG. 6 shows a fourth embodiment of the invention, in which the objective optical system 51 for performing observation in an oblique direction is attached to the distal end of the inserting portion 5 of the hard-type endoscope 1 according to the first embodiment.

In this embodiment, the first and second prisms 53 and 54 of the objective optical system 51 are coupled to each other, forming a prism unit 61. The spacer pipe 20 formed by cutting a long synthetic resin pipe molded by extrusion molding of synthetic resin materials containing an additive is interposed between the prism unit 61 and that one of the relay lenses 19 which is closest to the unit 61.

Since in this case, too, the spacer pipe 20 is interposed between each adjacent pair of the prism unit 61 and the relay lenses 19, thereby defining the spaces therebetween, the amount of light beams reflected from the inner periphery of the spacer pipes 20 and guided to the eye piece 12 can be reduced. Thus, a clear image with little flare can be transmitted, as in the first embodiment.

Figure 7:
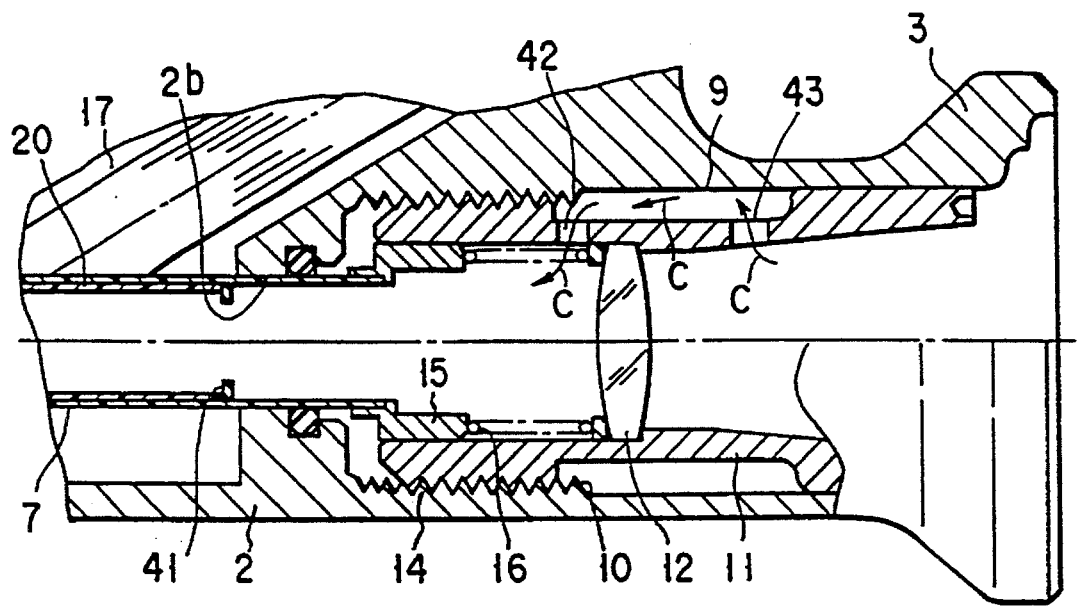
FIG. 7 is a longitudinal sectional view, showing an essential part of a modification of the hard-type endoscope of FIG. 6.
Figure 8:
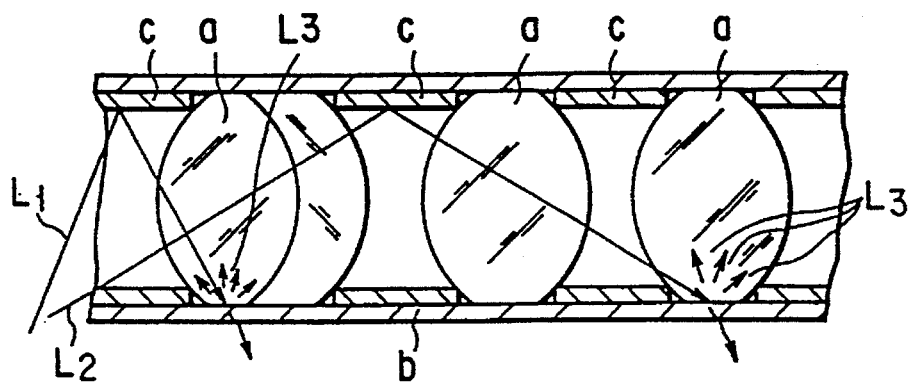
FIG. 8 is a longitudinal sectional view, showing an arrangement of lenses employed in the observation system of a conventional prior art hard-type endoscope.

FIG. 7 shows a modification of the hard-type endoscope 1. In the modification, a stop ring 41 is provided for the spacer pipe 20 located closest to the proximal end portion 2, thereby preventing the inner sheath 7 from moving into the spring-urging ring 15.

Moreover, a torsion coil spring 16 is interposed between the spring-urging ring 15 and the eye piece 12, thereby urging the eye piece 12 against the stepped engagement portion 13 of the unit case 11 of the eye-piece unit 8 and also urging the spring-urging ring 15.

Since the spacer pipe 20 is made of a synthetic resin, the degree of its thermal expansion is relatively high. The deformation of the pipe due to thermal expansion is absorbed in the torsion coil spring 16. Further, since the eye piece 12 is fixed to the stepped engagement portion 13 of the unit case 11 by means of the torsion coil spring 16, a process for, for example, adhering the eye piece 12 to the unit case 11 is not necessary. Thus, the eye-piece unit 8 can be assembled in a simple manner and at low cost.

In addition, since the unit case 11 for holding the eye piece 12 has the male screw portion 14 engaged with the female screw portion 10 formed in the inner periphery of the eye-piece mounting hole 9 of the proximal end portion 2, the focusing of the eye-piece unit 8 can easily be performed by rotating the unit case 11 to move the eye piece 12 in the axial direction.

Holes 42 and 43 are formed in those portions of the unit case 11 which are located in front of and to the rear of the eye piece 12. These holes 42 and 43 are used to clean the endoscope 1 after using the same. As is shown in FIG. 7, cleaning water flows through the hole 43 into a space defined between the unit case 11 and the peripheral wall of the eye-piece unit mounting hole 9 of the proximal end portion 2, and then into the inner sheath 7 through the hole 42 as shown by arrows c.

Since cleaning water is discharged only from the hole 42, at least a drop of water remains in the inner sheath 7 after cleaning the endoscope 1, thereby hazing the lenses or so. Thus, the field of view of the endoscope 1 is interrupted, and accordingly the used endoscope is prevented from being reused erroneously.

The invention is not limited to the above-described embodiments. The invention is applicable also to cameras or video cameras other than endoscopes, or binocular glasses. Furthermore, if a soft resin is used as the material of the spacer pipe 20 in the first embodiment or of the inner sheath 31 in the second embodiment, the invention can be applied to a soft-type endoscope.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A hard-type endoscope apparatus equipped with an inserting portion, an observation optical system inserted in the inserting portion, and a lens-barrel holding the observation optical system, comprising:

a molded tubular member provided at least in the lens-barrel along an optical path of the observation optical system, the tubular member being a single layer made of synthetic resin materials including an additive, the additive simultaneously forming matting irregularities on an inner surface of the tubular member at a time of molding the tubular member, so as to reduce a cost to manufacture the endoscope apparatus.

2. The apparatus according to claim 1, wherein the tubular member is formed as an extrusion molded member from the synthetic resin materials including the additive.

3. The apparatus according to claim 2, wherein the additive comprises glass.

4. The apparatus according to claim 2, wherein the additive comprises a glass fiber.

5. The apparatus according to claim 2, wherein the additive comprises a glass milled fiber.

6. The apparatus according to claim 2, wherein the additive comprises a powder.

7. The apparatus according to claim 2, wherein the tubular member is elongated along the optical path.

8. The apparatus according to claim 1, wherein the synthetic resin of the tubular member is black.

9. The apparatus according to claim 1, wherein the additive is dissolved in the synthetic resin materials forming the tubular member at the time of molding the tubular member by one of injection molding and extrusion molding.

10. A hard-type endoscope apparatus equipped with an inserting portion, an observation optical system inserted in the inserting portion, and a lens-barrel holding the observation optical system, comprising:

a plurality of lenses provided in the observation optical system; and a plurality of molded spacer pipes provided in the lens-barrel along an optical path of the observation optical system, for defining a space between each adjacent pair of the lenses along the optical path, the plurality of spacer pipes being made of a single layer of synthetic resin material including an additive, the additive simultaneously forming matting irregularities on an inner surface of the spacer pipes at a time of molding the spacer pipes, so as to reduce a cost to manufacture the endoscope apparatus.

* * * * *